(12) United States Patent
Lehtinen et al.

(10) Patent No.: US 11,160,558 B2
(45) Date of Patent: Nov. 2, 2021

(54) MULTIPLE OPEN/CLOSE OF RELOADABLE CLIP

(71) Applicant: Boston Scientific Limited, St. Michael (BB)

(72) Inventors: Laurie A. Lehtinen, Marlborough, MA (US); Shawn Ryan, Littleton, MA (US); Nishant Randhawa, Nagar (IN); Daniel Congdon, Wenham, MA (US)

(73) Assignee: BOSTON SCIENTIFIC LIMITED, St. Michael (BB)

( * ) Notice: Subject to any disclaimer, the term of this patent is extended or adjusted under 35 U.S.C. 154(b) by 491 days.

(21) Appl. No.: 15/709,048

(22) Filed: Sep. 19, 2017

(65) Prior Publication Data
US 2018/0078262 A1    Mar. 22, 2018

Related U.S. Application Data

(60) Provisional application No. 62/398,278, filed on Sep. 22, 2016.

(51) Int. Cl.
*A61B 17/128*  (2006.01)
*A61B 17/122*  (2006.01)
(Continued)

(52) U.S. Cl.
CPC ...... *A61B 17/1285* (2013.01); *A61B 17/1227* (2013.01); *A61B 2017/00477* (2013.01);
(Continued)

(58) Field of Classification Search
CPC ............ A61B 17/1285; A61B 17/1222; A61B 17/1227; A61B 2017/00477; A61B 2090/034
See application file for complete search history.

(56) References Cited

U.S. PATENT DOCUMENTS

2005/0143767 A1   6/2005 Kimura et al.
2007/0293875 A1*  12/2007 Soetikno ............ A61B 17/1227
                                                606/142
(Continued)

FOREIGN PATENT DOCUMENTS

CN       102525593       2/2015
CN       104490449       4/2015
(Continued)

*Primary Examiner* — Katherine M Rodjom
(74) *Attorney, Agent, or Firm* — Fay Kaplun & Marcin, LLP (57) ABSTRACT

A system for treating tissue includes an applicator including a catheter and a control member extending therethrough, the control member longitudinally movable relative to the catheter and including an abutment structure proximate a distal end thereof, and a clip assembly releasably coupleable to a distal end of the applicator, the clip assembly including a pair of clip arms, a proximal end of each of the clip arms slidably received within a channel of a capsule and configured to be releasably coupled to the distal end of the control member so that the clip arms are movable relative to the capsule between a tissue receiving configuration and a tissue clipping configuration, the capsule including proximal tabs movable between a biased non-engaging and an engaging configuration, in which the proximal tabs engage an engaging portion of the lumen of the catheter, when the abutment structure is received within the capsule.

10 Claims, 4 Drawing Sheets

(51) Int. Cl.
    *A61B 17/00*     (2006.01)
    *A61B 17/12*     (2006.01)
    *A61B 90/00*     (2016.01)

(52) U.S. Cl.
    CPC ............ *A61B 2017/12004* (2013.01); *A61B 2090/034* (2016.02)

(56) References Cited

U.S. PATENT DOCUMENTS

| | | | |
|---|---|---|---|
| 2008/0140089 A1* | 6/2008 | Kogiso | A61B 17/122 606/142 |
| 2011/0046651 A1 | 2/2011 | Cohen et al. | |
| 2013/0211432 A1 | 8/2013 | Terada | |
| 2013/0304095 A1 | 11/2013 | Barner et al. | |

FOREIGN PATENT DOCUMENTS

| | | |
|---|---|---|
| EP | 1829489 | 9/2007 |
| EP | 2371303 | 10/2011 |
| JP | 2003-339719 | 12/2002 |
| JP | 2006-198388 | 8/2006 |
| JP | 2007-196012 | 8/2007 |
| JP | 2015-186650 | 10/2015 |

\* cited by examiner

MULTIPLE OPEN/CLOSE OF RELOADABLE CLIP

PRIORITY CLAIM

The present disclosure claims priority to U.S. Provisional Patent Application Ser. No. 62/398,278 filed Sep. 22, 2016; the disclosure of which is incorporated herewith by reference.

BACKGROUND

Pathologies of the gastrointestinal (GI) system, the biliary tree, the vascular system, and other body lumens and hollow organs are often treated through endoscopic procedures, many of which require hemostasis to control internal bleeding. Hemostasis clips grasp tissue surrounding a wound and hold edges of the wound together temporarily to allow natural healing processes to permanently close the wound. Specialized endoscopic clipping devices are used to deliver the clips at the desired locations within the body after which the clip delivery device is withdrawn, leaving the clip within the body. In addition to providing hemostasis, endoscopic clipping devices may also be used to provide, for example, endoscopic marking and closure of luminal perforations.

SUMMARY

The present disclosure relates to a system for treating tissue, comprising an applicator and a clip assembly. The applicator includes a catheter and a control member extending therethrough, the catheter extending longitudinally from a proximal end to a distal end and including a lumen extending therethrough, the control member longitudinally movable relative to the catheter and including an abutment structure proximate a distal end thereof. The clip assembly is releasably coupleable to a distal end of the applicator and includes a pair of clip arms, each of the clip arms extending from a proximal end to a distal end, the proximal end of each of the clip arms slidably received within a channel of a capsule and configured to be releasably coupled to the distal end of the control member so that the clip arms are movable relative to the capsule between a tissue receiving configuration, in which distal ends of the clip arms are separated from one another, and a tissue clipping configuration, in which distal ends of the clip arms are moved toward one another, the capsule including proximal tabs movable between a biased non-engaging configuration, in which the proximal tabs extend into the channel, and an engaging configuration, in which the proximal tabs extend laterally outward relative to a longitudinal axis of the capsule to engage an engaging portion of the lumen of the catheter, the proximal tabs configured to move from the non-engaging configuration to the engaging configuration when the abutment structure is received within the capsule.

In an embodiment, the capsule may include distal tabs positioned distally of the proximal tabs.

In an embodiment, the distal tabs may be movable between a non-engaging configuration and an engaging configuration, in which the distal tabs extend laterally outward relative to an exterior surface of the capsule.

In an embodiment, the distal tabs may be formed via cut-outs through a wall of the capsule, the distal tabs extending from a distal end connected to the wall to a free proximal end extending toward the proximal end of the capsule.

In an embodiment, the capsule may include a plurality of fingers defining a proximal portion thereof, the proximal tabs extending from a proximal end of the fingers.

In an embodiment, the engagement portion of the lumen of the catheter may include a protrusion extending radially into the lumen.

In an embodiment, a distance between the proximal and distal tabs may be selected so that the proximal and distal tabs abut proximal and distal ends of the engagement portion of the catheter.

In an embodiment, the engagement portion of the lumen of the catheter may include a groove extending therein.

In an embodiment, the lumen may include a stop therealong, the stop configured to prevent the capsule from being movable proximally therepast.

In an embodiment, the abutment structure may include a protrusion extending radially from an exterior surface of the control member.

In an embodiment, the abutment structure may include a hypotube extending along a portion of a length of the control member.

In an embodiment, the distal end of the control member may be releasably connected to the proximal ends of the clip arms so that, when a proximal force on the control member exceeds a predetermined threshold value, the control member is disengaged from the clip arms.

The present disclosure also relates to a system for treating tissue, comprising a clip assembly and an applicator on to which the clip assembly is loadable. The clip assembly includes a pair of clip arms, each of the clip arms extending from a proximal end to a distal end, the proximal end of each of the clip arms slidably received within a channel of a capsule so that the clip arms are movable relative to the capsule between a tissue receiving configuration, in which distal ends of the clip arms are separated from one another, and a tissue clipping configuration, in which distal ends of the clip arms are moved toward one another, the channel of the capsule including an engagement portion at a proximal end thereof. The applicator includes a catheter and a control member extending therethrough, the catheter extending longitudinally from a proximal end to a distal end and including a lumen extending therethrough, distal tabs along a distal portion of the catheter movable between a non-engaging configuration and an engaging configuration, in which the distal tabs are moved away from a longitudinal axis of the catheter to engage the engagement portion.

In an embodiment, a distal portion of the catheter may define a plurality of fingers movable between the non-engaging and engaging configurations, the distal tabs extending laterally outward from a distal end of each of the fingers.

In an embodiment, the engagement portion may be a protrusion extending radially into the lumen so that, in the engaging configuration, the distal tabs engage a distal end of the engagement portion to prevent the capsule from being moved distally with respect to the catheter.

The present disclosure also relates to a method for treating tissue, comprising loading a first clip assembly, including a pair of clip arms with proximal ends slidably received within a capsule, on an applicator by coupling a control member of the applicator to the proximal ends of clip arms and by moving a catheter of the applicator over the capsule until proximal tabs of the capsule engage an engagement portion of the catheter, wherein the proximal tabs are moved from a non-engaging configuration, in which the proximal tabs extend into a channel of the capsule, to an engaging con-figuration, in which the proximal tabs extend laterally outward away from a longitudinal axis of the capsule, via an abutment surface of the control member when the abutment surface is received within the capsule, inserting the loaded clip assembly to a target site within a living body via a working channel of an endoscope, moving the first clip assembly between a tissue receiving configuration, in which distal ends of the clip arms are separated from one another, and a tissue clipping configuration, in which distal ends of the clip arms are moved toward one another, by moving the control member longitudinally relative to the catheter until a target tissue is gripped therebetween, as desired, and releasing the first clip assembly from the applicator by drawing the control member proximally relative to the yoke, beyond a predetermined threshold value, so that the control member disengages from the clip arms and the abutment surface is drawn out of the capsule to move the proximal ends toward the non-engaging configuration.

BRIEF DISCLOSURE

DETAILED DESCRIPTION

The present disclosure may be further understood with reference to the following description and the appended drawings, wherein like elements are referred to with the same reference numerals. The present disclosure relates to a clipping system and, in particular, relates to a reloadable endoscopic clipping system. Exemplary embodiments of the present disclosure describe a clip assembly that may be loaded onto a distal end of an applicator assembly prior to an endoscopic procedure. Once a clip has been deployed at a desired target area in the body, the applicator assembly may be reloaded with a new clip. In particular, the clip assembly includes a capsule configured to releasably engage a catheter of the applicator. The capsule may include a set of tabs moved into engagement with the catheter when an abutting structure is received within the capsule. When the abutting structure is removed therefrom, the capsule of the clip assembly may be separated from the applicator. It should be noted that the terms "proximal" and "distal," as used herein, are intended to refer to a direction toward (proximal) and away from (distal) a user of the device.

Figure 1:
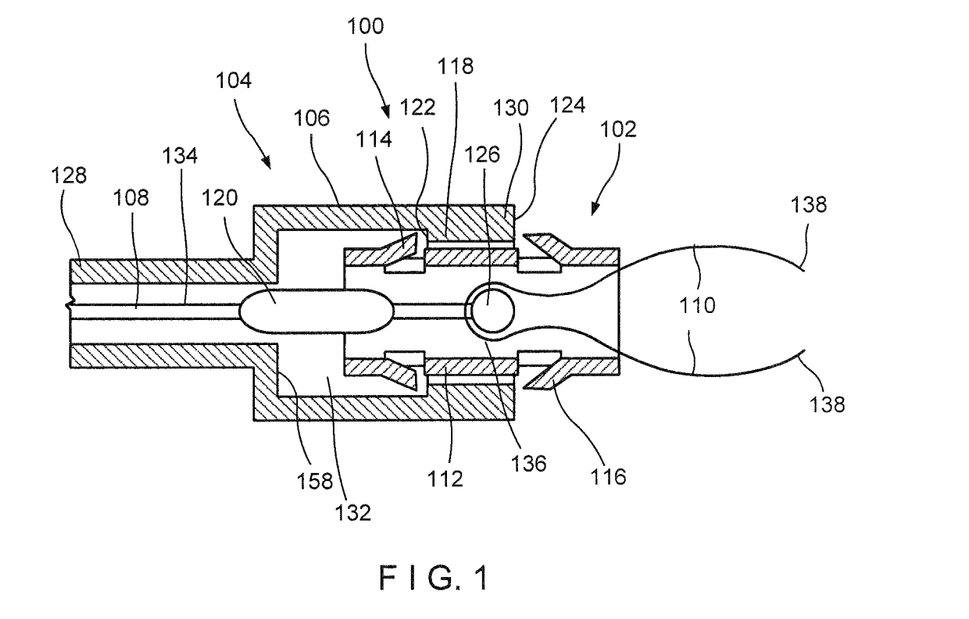
FIG. 1 shows a longitudinal cross-sectional view of a system according to an exemplary embodiment of the present disclosure.
Figure 2:
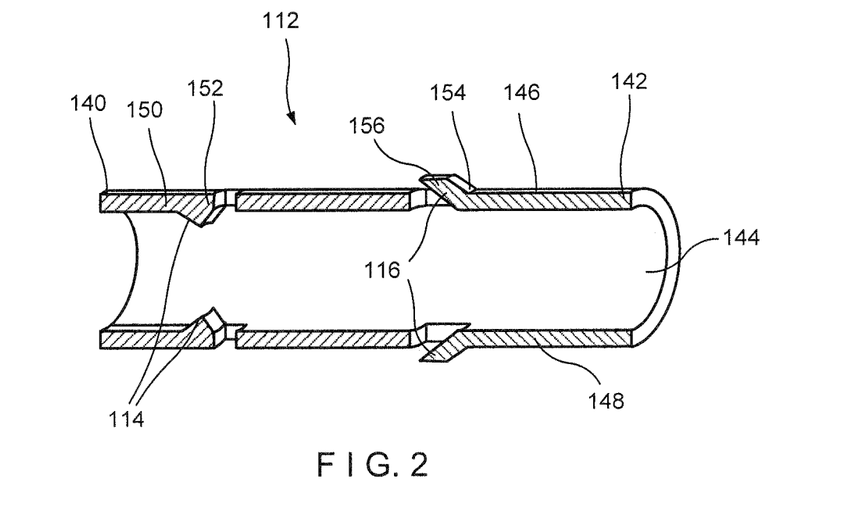
FIG. 2 shows a longitudinal cross-sectional view of a capsule of the system according to FIG. 1.

As shown in FIGS. 1-2, a system 100 according to an exemplary embodiment of the present disclosure comprises a clip assembly 102 loadable onto a distal portion of an applicator 104 prior to insertion of the system 100 into a living body for the clipping of target tissue. The applicator 104 and the clip assembly 102 are configured so that, after deployment of the clip assembly 102 in the living body, a new clip assembly 102 may be loaded onto the applicator 104 so that the same applicator 104 may be used to a deliver a new clip assembly to a second portion of target tissue in the living body. The applicator 104 may include a catheter 106 and a control member 108 (e.g., a control wire) extending therethrough. The clip assembly 102 of this embodiment includes a pair of arms 110 slidably received within a capsule 112. The capsule 112 includes proximal and distal tabs 114, 116 tabs for engaging an engagement portion 118 of the catheter 106. In particular, the proximal tabs 114 may be biased laterally inward toward a longitudinal axis of the capsule 112 and may be moved toward an engagement configuration when an abutting structure 120 of the control member 108 is received within the capsule 112. Thus, to load the clip assembly 102 onto the applicator 104, the catheter 106 is moved distally over the capsule 112 while the control member 108 is moved distally through the capsule 112 to connect to a proximal end of the clip arms 110. As the control member 108 is moved distally through the capsule 112, the abutting structure 120 is moved into the capsule 112, moving the proximal tabs 114 laterally outward toward the engagement configuration to engage the engagement structure 118. In use, the proximal tabs 114 engage a proximal end 122 of the engagement structure 118 while the distal tabs 116 engage a distal end 124 of the engagement structure 118 so that upon engagement, the capsule 112 is fixed with respect to the catheter 106. Thus, by moving the control member 108 longitudinally relative to the catheter 106 and capsule 112, the clip arms 110 may be moved between an open, tissue receiving configuration and a closed, tissue gripping configuration. When it is desired to deploy the clip assembly 102 from applicator 104, the control member 108 may be withdrawn from the capsule 112 to remove the abutting structure 120 from between the proximal tabs 114, permitting the proximal tabs 114 to disengage the engagement feature 118.

The applicator 104 includes the catheter 106 and a control member 108 extending therethrough. The catheter 106 may be connected to a distal end of a flexible member (not shown) which connects the catheter 106 to a handle member at a proximal end thereof. The flexible member may be formed, for example, as a coil of wire through which the control member 108 extends. As would be understood by those skilled in the art, the coil of wire preferably has sufficient flexibility to be passed through even tortuous paths of living body and, in this embodiment, is sized and shaped to permit it to be passed through a working channel of a flexible endoscope or other insertion device. Although the flexible member is shown and described as a coil of wire, any other suitable flexible structure may be employed so long as the flexible member is capable of providing a force in compression sufficient to counter the tension to be placed on the control member 108 from the clip assembly 102.

The catheter 106 extends longitudinally from a proximal end 128 to a distal end 130 and including a lumen 132 extending therethrough. The lumen 132 is sized and shaped to receive the capsule 112 therein. The lumen 132 includes the engagement portion 118 along a distal section thereof. The engagement portion 118 may be configured as a protrusion extending radially inward toward a longitudinal axis of the catheter 106. The engagement portion 118 extends along a length of the lumen 132 from a proximal end 122 to a distal end 124. The distal end 124 of the engagement portion 118 may coincide, for example, with the distal end 130 of the catheter 106. Although the engagement portion 118 is described and shown as a protrusion, the engagement portion 118 may be configured as any structure or feature which reduces a diameter or cross-sectional area of the lumen 132 along the length of the engagement structure 118. The lumen 132 may also include a stop 158 configured as, for example, a shoulder preventing a capsule 112 received within the lumen 132 from being moved proximally therepast.

The control member 108 extends through the catheter 106 and the flexible member from an enlarged distal end 126 to a proximal end, which may be connected to an actuator along the handle member. Thus, the control member 108 may be moved longitudinally with respect to the flexible member and the catheter 106. In one embodiment, the enlarged distal end 126 is configured as a ball. Proximally of the enlarged distal end 126, the control member 108 includes the abutting structure 120 along a portion of a length thereof. The abutting structure 120 should be spaced from the enlarged distal end 126 by a distance sufficient to permit the enlarged distal end 126 to engage the proximal end of the clip arms 110 while the abutting structure 120 is received within the capsule 112. The abutting structure 120 extends radially outward from an exterior surface 134 of the control member 108 and along a portion of a length of the control member 108. In another embodiment, the abutting structure 120 may be configured as a hypotube or other structure fixed over a portion of a length of the control member 108. Cross-sectional areas of both the abutting structure 120 and the enlarged distal end 126 are larger than a cross-sectional area of a remaining portion of the control member 108. The cross-sectional area of the abutting structure 120 is selected so that, when received within the capsule 112, moves the proximal tabs 114 to the engaging configuration, as will be described in further detail below. A length of the abutting structure 120 is selected so that, the abutting structure 120 maintains an engagement with the tabs 114, holding the proximal tabs 114 in the engaging configuration, while the clip arms 110 are moved relative to the capsule 106 between the tissue receiving and tissue gripping configurations and until it is desired to deploy the clip assembly 102 from applicator 104.

The clip assembly 102 includes the pair of clip arms 110, proximal ends 136 of which are slidably received within the capsule 106 to move the clip assembly 102 between the tissue receiving configuration and the tissue gripping configuration. Each of the clip arms 110 extends from a proximal end 136 to a distal end 138. Proximal ends 136 of the clip arms 110 may be connected to one another and configured to be releasably connected to the enlarged distal end 126 of the control member 108 so that the control member 108 may be moved longitudinally with respect to the capsule 112 to move the clip assembly 102 between the tissue receiving and gripping configurations. The clip arms 110 of this embodiment are biased so that the distal ends 138 thereof move apart from one another into the tissue receiving configuration when not drawn into the capsule 112. When drawn into the capsule 112, the capsule 112 constrains the clip arms 110, holding distal ends 138 thereof together in the tissue gripping configuration. The clip arms 110 may be formed via a single component forming two arms or via two separate pieces.

The clip arms 110 may include gripping features configured to facilitate the gripping of tissue therebetween. For example, the distal ends 138 of the clip arms 110 may include tips extending laterally inward toward one another and/or teeth, protrusions, spikes or other structures configured to grip tissue between the distal ends 138 of the clip arms 110. The clip arms 110 may also include a locking feature configured to lock the clip arms 110 in the tissue gripping configuration, once a desired target tissue has been gripped via the clip arms 110. In one embodiment, the clip arms 110 may include a locking tab extending laterally outward therefrom. This locking tab may be configured to engage a portion of the capsule 112 when the clip arms 110 have been drawn into the capsule 112 by a predetermined distance. For example, the locking tabs may be received within correspondingly sized, shaped and positioned locking windows extending laterally through a wall of the capsule 112 to lock the clip arms 110 relative to the capsule 112, in the tissue gripping configuration.

In one exemplary embodiment, the proximal ends 136 of the clip arms 110 are connected to one another via a yoke (not shown) slidably received within the capsule 112 and configured to receive the enlarged distal end 126 of the control member 108 therein. The yoke may include a longitudinal slot extending thereinto from a proximal end thereof. In one example, the longitudinal slot is configured as a socket for receiving a ball-shaped enlarged distal end 126. Opposed portions of the yoke may be spreadable to receive the enlarged distal therepast and biased so that, once the enlarged distal end 126 passes distally into the socket, the opposed portions spring back to lock the enlarged distal end 126 therein, coupling the control member 108 to the clip arms 110. Thus, longitudinal movement of the control member 108 relative to the capsule 112 may control movement of the clip arms 110 between the tissue receiving and the tissue gripping configurations.

The capsule 112 extends longitudinally from a proximal end 140 to a distal end 142 and includes a channel 144 extending longitudinally therethrough. The channel 144 is sized and shaped to receive the proximal ends 136 and at least a proximal portion of the clip arms 110 therein. As described above, the capsule 112 includes proximal tabs 114 proximate the proximal end 140 and distal tabs 116 distal of the proximate tabs 114. In this embodiment, the proximal tabs 114 are movable between a non-engaging configuration and an engaging configuration. The proximal tabs 114 are biased toward the non-engaging configuration, in which the proximal tabs 114 extend laterally inward, toward the longitudinal axis of the capsule. In the engaging configuration, the proximal tabs 114 extend laterally outward, beyond an exterior surface 146 of the capsule 112. The proximal tabs 114 should be sized and shaped so that, when the abutting structure 120 is received within the channel 144 of the capsule 112, the proximal tabs 114 are moved from the non-engaging configuration to the engaging configuration. In one embodiment, the proximal tabs 114 extend from a proximal end 150 connected to a wall 148 of the capsule 112 to a free distal end 152 movable between the non-engaging and engaging configurations. The proximal end 150 may be integrally formed with the wall 148 of the capsule 112.

The distal tabs 116 may also be movable between a non-engaging configuration and an engaging configuration. The distal tabs 116, however, are biased toward the engaging configuration, in which the distal tabs 116 extend laterally outward, away from a longitudinal axis of the capsule 112 and beyond the exterior surface 146 thereof. In one embodiment, the distal tabs 116 are formed via cut-outs extending through a wall 148 of the capsule 112, the cut-outs being angled laterally outward, away from the exterior surface 146 and toward the proximal end 140 of the capsule 112 in the engaging configuration. In other words, the distal tabs 116 extend from a distal end 154 which remains connected to the wall 148 of the capsule 112 and a free proximal end 156 movable between the non-engaging and engaging configuration. In the non-engaging configuration, the distal tabs 112 may be flush with the exterior surface 146.

A distance between the proximal and distal tabs 114, 116 corresponds to a length of the engagement portion 118 along the interior of the lumen 132 of the catheter 106. In particular, the distance between the proximal and distal tabs 114, 116 should be only slightly greater than the length of the engagement portion 118 so that, when the catheter 106 and the capsule 112 are engaged to one another, the engagement portion 118 is received between the proximal and distal tabs 114, 116 and is prevented from any substantial movement relative to the capsule 112. Movement of the proximal and distal tabs 114, 116 between the non-engaging and engaging configurations during loading and use of the clip assembly 102, will be described in further detail below.

Although the distal tabs 116 are described and shown as being movable between the non-engaging and engaging configurations, in another embodiment, the distal tabs 116 may be fixed in the engaging configuration. In this embodiment, the distal tabs 116 engage the engagement portion 118 during loading of the clip assembly 102. In particular, the distal tabs 116 abut the distal end 124 of the engagement portion 118, preventing further distal movement of the catheter 106 relative thereto during loading of the clip assembly 102. Thus, when the distal tabs 116 engage the engagement portion 118, the proximal tabs 114 extend proximally of the proximal end 122 of the engagement portion 118 and are permitted to move toward the engaging configuration.

Prior to being loaded on the applicator 104, the clip assembly 102 is stored, for example, in a cartridge configured to facilitate loading of the clip assembly on the applicator 104. The cartridge defines a space therein sized and shaped to house the clip assembly 102. The clip assembly 102 may be housed within the cartridge in the tissue receiving configuration. In one embodiment, the cartridge constrains the distal tabs 116 of the capsule 112 toward the non-engaging configuration. The cartridge includes a proximal opening through which catheter 106 and the control member 108 may be inserted to be coupled to the capsule 112 and the clip arms 110, respectively. The cartridge holds the clip assembly 102 in position to facilitate loading onto the applicator 104.

An exemplary method for loading the clip assembly 102 to the applicator 104 comprises inserting the catheter 106 and the control member 108 into the cartridge so that the control member 108 passes through the channel 144 of the capsule 112 while the catheter 106 is moved distally over the capsule 112. As described above, the distal tabs 116 may be constrained in the non-engaging configuration by the cartridge so that the catheter 106 may be moved distally over the distal tabs 116. Thus, once the catheter 106 is mounted over the capsule 112, a surface of the lumen 132 of the catheter 106 constrains the distal tabs 116 in the non-engaging configuration. In other words, the engagement portion 118 extends over the distal tabs 116 preventing the distal tabs 116 from moving toward the engaging configuration. As the enlarged end 126 is passed distally through the capsule 112 to releasably coupled to the proximal ends 136 of the clip arms 110, the abutment structure 120 is received within the channel 144 of the capsule 112, moving the proximal tabs 114 from the biased non-engaging configuration to the engaging configuration. The proximal tabs 114 extend proximally of the engagement structure 118.

Once the catheter 106 is mounted over the capsule 112 and the enlarged distal end 126 is coupled to the clip arms 110 (e.g., via a yoke), the control member 108 may be moved proximally with respect to the catheter 106. This proximal motion of the control member 108 moves the clip assembly 102 toward the tissue receiving configuration. Proximal motion of the control member 108 may also draw the capsule 112 further proximally into the lumen 132 of the catheter 106, toward an insertion configuration. The capsule 112 may be moved proximally until the stop 158 prevents further proximal movement thereof. The clip assembly 102 may be drawn out of the cartridge in this insertion configuration. Since the capsule 112 is drawn farther proximally into the catheter 106 in this insertion configuration, a greater portion of the clip arms 110 is covered during insertion of the clip assembly 102 into a living body, helping to prevent damage to a working channel through which the clip assembly 102 is inserted or a surrounding tissue.

In use, after the clip assembly 102 has been loaded onto the applicator 104, the clip assembly 102 is inserted through a working channel of an endoscope (or any other insertion device) and inserted into the body (e.g., through a natural body lumen) to a site adjacent to a target portion of tissue to be clipped. The clip assembly 102 is inserted to the target tissue in the insertion configuration (e.g., with the catheter 106 constraining the distal tabs 116 toward the non-engaging configuration) to reduce damage and facilitate its passage through the working channel. Upon reaching the site of the target tissue, the clip assembly 102 is advanced out of the distal end of the working channel by moving the control member 108 distally relative to the catheter 106 extending the clip arms 110 distally out of the capsule 124 and moving the clip arms 110 to the tissue receiving configuration. Since, in the insertion configuration, the proximal tabs 114 of the capsule 112 are proximal of the engagement portion 118 of the catheter 106 and the distal tabs 116 are constrained in the non-engaging configuration, the distal motion of the control member 108 may also move the capsule 112 distally with respect to the catheter 106 until the proximal tabs 114 abut the proximal end 122 of the engagement portion 118 and/or the distal tabs 116 extend distally of the distal end 124 of the engagement portion 118. As the distal tabs 116 are moved past the distal end 124 of the engagement portion 118, the distal tabs 116 are permitted to revert to their biased engaging configuration. Thus, in this engaging configuration, the proximal tabs 114 extend proximally of the engagement portion 118 while the distal tabs 116 extend distally of the engagement portion 118. As described above, the distance between the proximal and distal tabs 114, 116 is selected so that, in this engaging configuration, the capsule 112 is substantially longitudinally fixed with respect to the catheter 106.

Once the capsule 112 and catheter 106 are engaged with one another, the clip arms 110 are extended distally out of the capsule 112 toward the tissue receiving configuration. The control member 108 may then be advanced distally and withdrawn proximally to move the clip assembly 102 between the tissue receiving and the tissue gripping configurations until a target portion of tissue is received between the distal ends 138 of the clip arms 110, as desired. The clip arms 110 may then be moved toward the tissue gripping configuration by moving the control member 108 proximally relative to the catheter 106. Once the clip assembly 102 is in the tissue gripping configuration, the control member 108 may be drawn further proximally to lock the clip arms 110 with respect to the capsule 112. To deploy the clip assembly 102, the control member 108 is drawn even further proximally until a force exerted thereon exceeds a predetermined threshold value, causing the enlarged distal end 126 to disengage the proximal ends 136 of the clip arms 110. Disengagement of the control member 108 from the clip arms 110 permits the control member 108 to be drawn proximally out of the capsule 112 so that the abutment structure 120 is removed therefrom. Removal of the abutment structure 120 causes the proximal tabs 114 to revert to their biased non-engaging configuration, so that the proximal tabs 114 disengage the engagement portion 118. Thus, the applicator 104 may be withdrawn proximally from the body, leaving the clip assembly 102 clipped over the target tissue. If so desired, a new clip assembly 102 is then loaded onto the applicator 104, in the same manner as described above, so that the device may then be used to clip a second portion of tissue. This process may be repeated using the same applicator 104 as many times as needed or desired.

Although the engagement portion 118 of the catheter 106 is described as extending over the distal tabs 116 to constrain the distal tabs 116 toward the non-engaging configuration in the insertion configuration, in another embodiment, the proximal and distal tabs 114, 116 may both engage the engagement portion 118 during loading of the clip assembly 102 so that the capsule 112 is substantially longitudinally fixed relative to the catheter 106. In this embodiment, the clip assembly 102 may be inserted into the body in the tissue gripping configuration so that the capsule 112 is fixed relative to the catheter 106 until deployment of the clip assembly 102.

Figure 3:
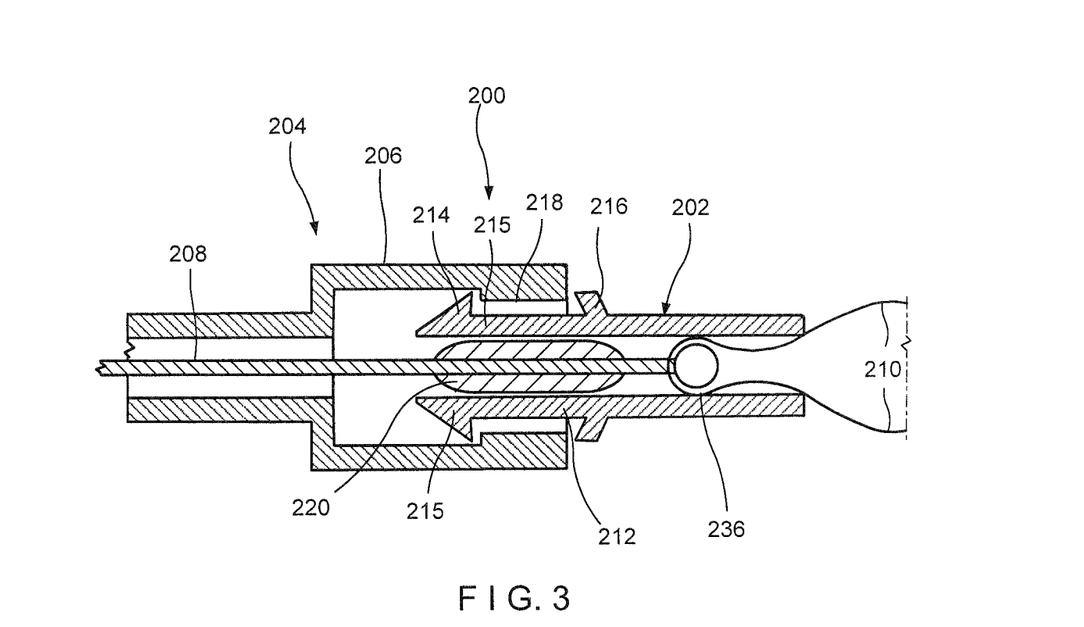
FIG. 3 shows a longitudinal cross-sectional view of a system according to another exemplary embodiment of the present disclosure, in an engaging configuration.
Figure 4:
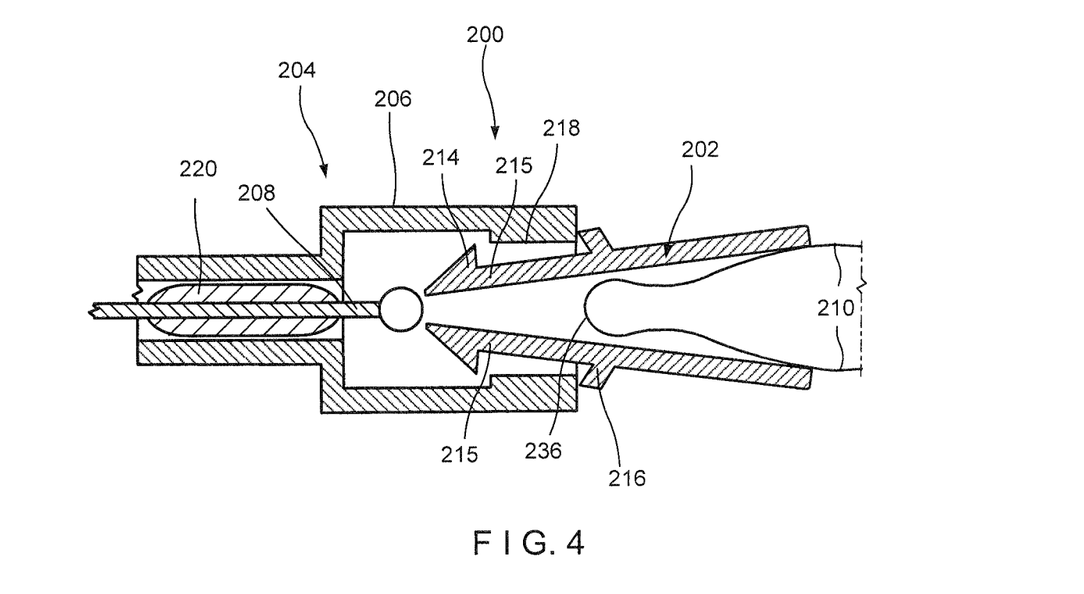
FIG. 4 shows a longitudinal cross-sectional view of the system according to FIG. 3, in a non-engaging configuration.

As shown in FIGS. 3-4, a system 200 according to another exemplary embodiment of the present disclosure may be substantially similar to the system 100, as described above, comprising an applicator 204 which may be loaded with a clip assembly 202. The applicator 204 may be substantially similar to the applicator 104, including a catheter 206 having an engagement portion 218 and a control member 208 including an abutment structure 220 extending therethrough. The clip assembly 202 is also substantially similar to the clip assembly 102, including a pair of clip arms 210, proximal ends 236 ends of which are slidably received within a capsule 212. Similarly to the capsule 112, the capsule 212 includes proximal tabs 214 and distal tabs 216. The capsule 212, however, defines a plurality of fingers 215 along a proximal portion thereof with the proximal tabs 214 extending laterally outward therefrom. The fingers 215 are biased radially inward toward a longitudinal axis of the capsule 212—i.e., toward a non-engaging configuration. The proximal tabs 214 themselves are not movable. When the abutment structure 220 is received within the capsule 212, the fingers 215 are moved radially outward toward an engaging configuration, so that the proximal tabs 214 engage the engagement portion 218. The clip assembly 202 may be loaded, used and deployed in a manner substantially similar to the method described above with respect to the system 100.

Figure 5:
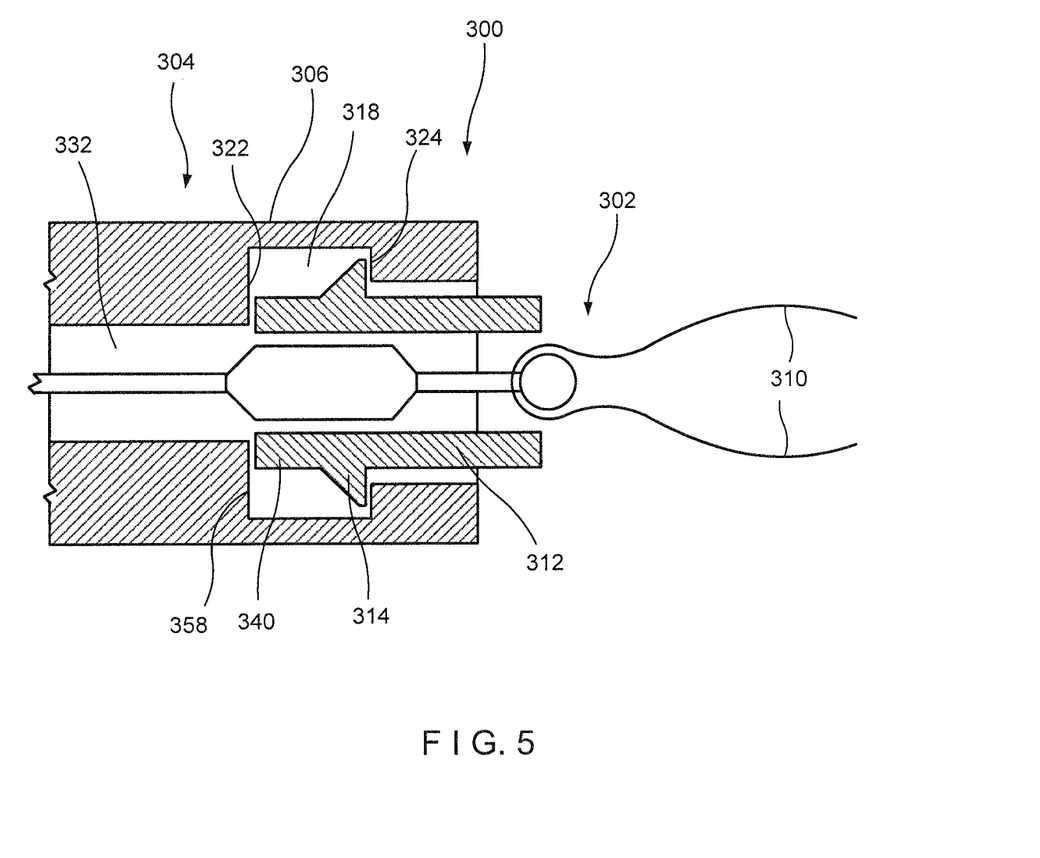
FIG. 5 shows a longitudinal cross-sectional view of a system according to yet another exemplary embodiment of the present disclosure.

According to another embodiment, as shown in FIG. 5, a system 300 may be substantially similar to the systems 100, 200, as described above, the system 300 comprising an applicator 304 onto which a clip assembly 302 may be loaded. An engagement portion of a catheter 306 of the applicator 304, however, is configured as a groove 318 extending about a lumen 332 of the catheter 306. The groove 318 extends from a proximal end 322 that coincides with a stop or shoulder 358 of the lumen 332, which prevents a capsule 312 of the clip assembly 302 from being moved proximally therepast, to a distal end 324. A cross-sectional area (e.g., diameter) of a portion of the lumen 332 distal of the groove 318 may substantially correspond to a cross-sectional area (e.g., diameter) of an exterior of the capsule 312.

In this embodiment, the capsule 312 does not require distal tabs. Rather, the capsule 312 is engaged to the catheter 306 when the proximal end 340 of the capsule 312 abuts the shoulder 358 and proximal tabs 314 are positioned within the groove 318, proximal of the distal end 324 of the groove 318, so that the proximal tabs 314 are permitted to move toward an engaging configuration to be received within the groove 318, when an abutment structure 320 of a control member 308 is received within the capsule 312. In this configuration, the capsule 312 is substantially fixed relative to the catheter 306 so that clip arms 310 may be moved between a tissue receiving and a tissue gripping configuration, until the clip assembly 302 is deployed from. The clip assembly 302 may be loaded, used and deployed in a manner substantially similar to the systems 100, 200 described above.

Figure 6:
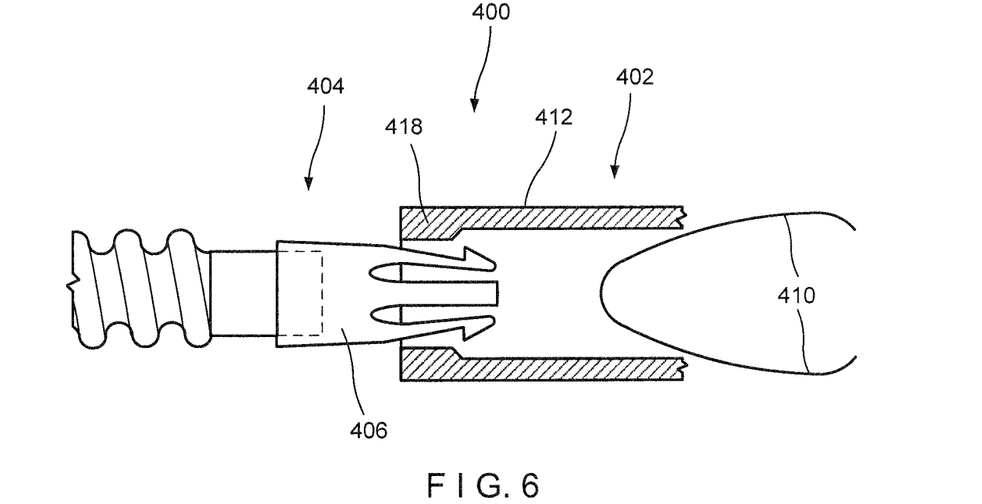
FIG. 6 shows a longitudinal cross-sectional view of a system according to another exemplary embodiment of the present disclosure, in a non-engaging configuration.
Figure 7:
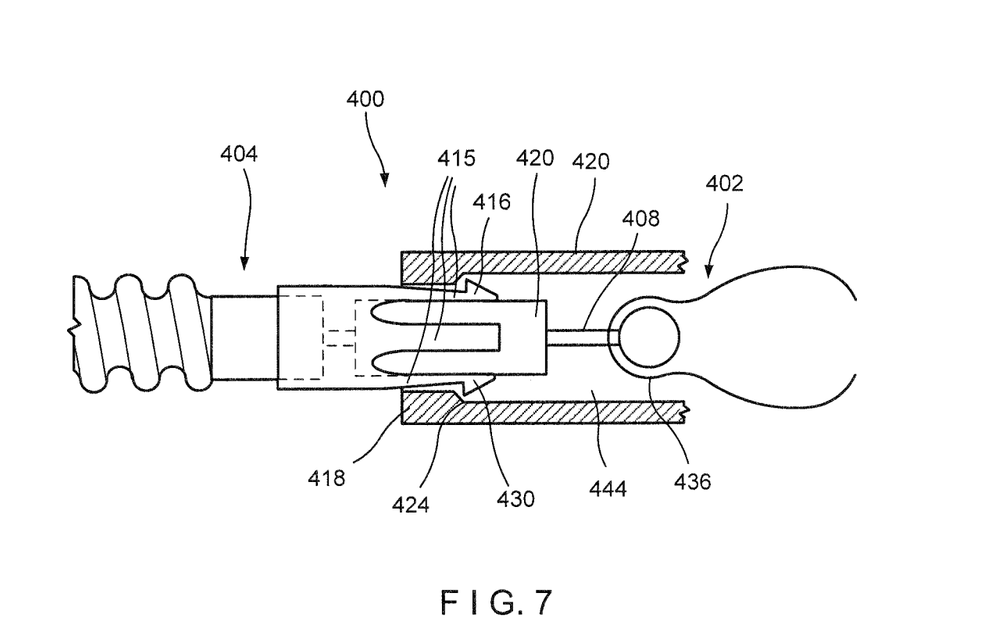
FIG. 7 shows a longitudinal cross-sectional view of the system according to FIG. 6, in an engaging configuration.

As shown in FIGS. 6-7, a system 400 according to another exemplary embodiment of the present disclosure may be substantially similar to the systems 100-300 described above, comprising an applicator 404 onto which a clip assembly 402 may be loaded. Similar to the applicators 104-304 described above, the applicator 404 includes a catheter 406 through which a control member 408 having an abutment structure 420 extends. Similarly to the clip assemblies 102-302, the clip assembly 402 may include clip arms 410, proximal ends 436 of which are slidably received within a capsule 412. Rather than the capsule 412 being received within the catheter 406, however, the catheter 406 is received within a channel 444 of the capsule 412 during loading of the clip assembly 402. A proximal portion of the channel 444 of the capsule 412 includes an engagement portion 418 extending radially inward resulting in, for example, a reduced diameter portion.

A distal portion of the catheter 406 defines a plurality of fingers 415 extending therealong. The fingers 415 are biased toward a non-engaging configuration in which they extend radially inward toward a longitudinal axis of the capsule 412. Distal tabs 416 extend laterally outward from distal ends 430 of the fingers 415 so that, when the abutment structure 420 is received within the catheter 416, the fingers 415 are moved radially outward toward an engaging configuration so that the distal tabs 416 engage the distal end 424 of the engagement portion 418, as shown in FIG. 7. In another embodiment, the distal tabs 416 themselves may be movable between a non-engaging and engaging configuration so that plurality of fingers 415 are not required. The system 400 may be used in manner substantially similar to the systems 100-300 described above.

It will be apparent to those skilled in the art that various modifications may be made in the present disclosure, without departing from the scope of the disclosure.

What is claimed is:

1. A system for treating tissue, comprising:
    an applicator including a catheter and a control member extending therethrough, the catheter extending longitudinally from a proximal end to a distal end and including a lumen extending therethrough, the control member longitudinally movable relative to the catheter and including an abutment structure proximate a distal end thereof;
    a first clip assembly releasably coupleable to a distal end of the applicator, the first clip assembly including a pair of first clip arms, each of the first clip arms extending from a proximal end to a distal end, the proximal end of each of the first clip arms slidably received within a channel of a first capsule and configured to be releasably coupled to the distal end of the control member so that the first clip arms are movable relative to the first capsule between a tissue receiving configuration, in which distal ends of the first clip arms are separated from one another, and a tissue clipping configuration, in which distal ends of the first clip arms are moved toward one another, the first capsule including proximal tabs movable between a biased non-engaging configuration, in which the proximal tabs extend into the channel of the first capsule, and an engaging configuration, in which the proximal tabs extend laterally outward relative to a longitudinal axis of the first capsule to engage an engaging portion of the lumen of the catheter, the proximal tabs configured to move from the non-engaging configuration to the engaging configuration when the abutment structure is received within the first capsule; and a second clip assembly configured to be releasably coupled to the distal end of the applicator after the first clip assembly has been deployed therefrom, the second clip assembly including a pair of second clip arms, each of the second clip arms extending from a proximal end to a distal end, the proximal end of each of the second clip arms slidably received within a channel of a second capsule and configured to be releasably coupled to the distal end of the control member so that the second clip arms are movable relative to the second capsule between a tissue receiving configuration, in which distal ends of the second clip arms are separated from one another, and a tissue clipping configuration, in which distal ends of the second clip arms are moved toward one another, the second capsule including proximal tabs movable between a biased non-engaging configuration, in which the proximal tabs extend into the channel of the second capsule, and an engaging configuration, in which the proximal tabs extend laterally outward relative to a longitudinal axis of the second capsule to engage an engaging portion of the lumen of the catheter, the proximal tabs configured to move from the non-engaging configuration to the engaging configuration when the abutment structure is received within the second capsule.

2. The system of claim 1, wherein the first capsule includes distal tabs positioned distally of the proximal tabs.

3. The system of claim 2, wherein the distal tabs are movable between a non-engaging configuration, in which the distal tabs extend laterally outward relative to an exterior surface of the first capsule.

4. The system of claim 3, wherein the distal tabs are formed via cut-outs through a wall of the first capsule, the distal tabs extending from a distal end connected to the wall to a free proximal end extending toward the proximal end of the first capsule.

5. The system of claim 2, wherein a distance between the proximal and distal tabs is selected so that the proximal and distal tabs abut proximal and distal ends of the engagement portion of the catheter.

6. The system of claim 1, wherein the engagement portion of the lumen of the catheter includes a protrusion extending radially into the lumen.

7. The system of claim 1, wherein the lumen includes a stop therealong, the stop configured to prevent the first capsule from being movable proximally therepast.

8. The system of claim 1, wherein the abutment structure includes a protrusion extending radially from an exterior surface of the control member.

9. The system of claim 1, wherein the abutment structure includes a hypotube extending along a portion of a length of the control member.

10. The system of claim 1, wherein the distal end of the control member is releasably connected to the proximal ends of the first clip arms so that, when a proximal force on the control member exceeds a predetermined threshold value, the control member is disengaged from the first clip arms.

\* \* \* \* \*